United States Patent
Truschel (10) Patent No.: US 11,291,786 B2
(45) Date of Patent: Apr. 5, 2022

(54) REDUCING HYPERCAPNIC RESPIRATORY FAILURE DURING MECHANICAL VENTILATION

(71) Applicant: KONINKLIJKE PHILIPS N.V., Eindhoven (NL)

(72) Inventor: William Anthony Truschel, Oakmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1242 days.

(21) Appl. No.: 15/124,359

(22) PCT Filed: Mar. 3, 2015

(86) PCT No.: PCT/IB2015/051528
§ 371 (c)(1),
(2) Date: Sep. 8, 2016

(87) PCT Pub. No.: WO2015/136405
PCT Pub. Date: Sep. 17, 2015

(65) Prior Publication Data
US 2017/0014588 A1 Jan. 19, 2017

Related U.S. Application Data

(60) Provisional application No. 61/951,061, filed on Mar. 11, 2014.

(51) Int. Cl.
*A61M 16/00* (2006.01)
*A61M 16/04* (2006.01)
(Continued)

(52) U.S. Cl.
CPC ...... *A61M 16/0069* (2014.02); *A61M 16/024* (2017.08); *A61M 16/04* (2013.01);
(Continued)

(58) Field of Classification Search
CPC ............ A61M 16/0069; A61M 16/024; A61M 16/04; A61M 16/0666; A61M 16/0875; A61M 16/1075; A61M 16/16; A61M 2016/0015; A61M 2016/0036; A61M 2016/103; A61M 2205/15;
(Continued)

(56) References Cited

U.S. PATENT DOCUMENTS 3,789,837 A * 2/1974 Philips ................ A61M 16/022
128/202.22
6,041,780 A 3/2000 Richard
(Continued)

FOREIGN PATENT DOCUMENTS

WO WO9841146 A1 9/1998
WO WO2008100859 A2 8/2008
(Continued)

*Primary Examiner* — Samchuan C Yao
*Assistant Examiner* — Cana A Gallegos
(74) *Attorney, Agent, or Firm* — Daniel H. Brean (57) ABSTRACT

Systems and methods provide respiratory therapy to a subject through a pressurized flow of breathable gas. Timing and other characteristics of pressure and flow levels provided during inhalations and exhalations are adjusted in order to increase the volumetric rate of expulsion of CO2.

15 Claims, 5 Drawing Sheets

(51) Int. Cl.
  *A61M 16/06* (2006.01)
  *A61M 16/08* (2006.01)
  *A61M 16/10* (2006.01)
  *A61M 16/16* (2006.01)
(52) U.S. Cl.
  CPC .... *A61M 16/0666* (2013.01); *A61M 16/0875* (2013.01); *A61M 16/1075* (2013.01); *A61M 16/16* (2013.01); *A61M 2016/0015* (2013.01); *A61M 2016/0036* (2013.01); *A61M 2016/103* (2013.01); *A61M 2205/15* (2013.01); *A61M 2205/3334* (2013.01); *A61M 2205/505* (2013.01); *A61M 2205/52* (2013.01); *A61M 2230/005* (2013.01); *A61M 2230/04* (2013.01); *A61M 2230/10* (2013.01); *A61M 2230/14* (2013.01); *A61M 2230/202* (2013.01); *A61M 2230/42* (2013.01); *A61M 2230/432* (2013.01); *A61M 2230/60* (2013.01)
(58) Field of Classification Search
  CPC .... A61M 2205/3334; A61M 2205/505; A61M 2205/52; A61M 2230/005; A61M 2230/04; A61M 2230/10; A61M 2230/14; A61M 2230/202; A61M 2230/42; A61M 2230/432; A61M 2230/60
  See application file for complete search history.

(56) References Cited

U.S. PATENT DOCUMENTS

| | | |
|---|---|---|
| 2002/0104536 A1 | 8/2002 | Richey, II |
| 2005/0109340 A1* | 5/2005 | Tehrani ............... A61M 16/026 128/204.21 |
| 2006/0000475 A1 | 1/2006 | Matthews |
| 2006/0155206 A1 | 7/2006 | Lynn |
| 2008/0202525 A1* | 8/2008 | Mitton ............... A61M 16/104 128/204.22 |
| 2013/0247914 A1* | 9/2013 | Truschel ............. A61M 16/161 128/204.23 |
| 2013/0253359 A1 | 9/2013 | Emtell |

FOREIGN PATENT DOCUMENTS

| | | |
|---|---|---|
| WO | WO2013027137 A1 | 2/2013 |
| WO | WO2014027267 A2 | 2/2014 |

\* cited by examiner

REDUCING HYPERCAPNIC RESPIRATORY FAILURE DURING MECHANICAL VENTILATION

CROSS-REFERENCE TO RELATED APPLICATIONS

This patent application claims the priority benefit under 35 U.S.C. § 371 of international patent application no. PCT/IB2015/051528, filed Mar. 3, 2015, which claims the priority benefit under 35 U.S.C. § 119(e) of U.S. Provisional Application No. 61/951,061 filed on Mar. 11, 2014, the contents of which are herein incorporated by reference.

BACKGROUND OF THE INVENTION

1. Field of the Invention

The present disclosure pertains to systems and methods for providing respiratory therapy to subjects. In particular, the present disclosure pertains to adjusting the timing of delivery for a pressurized flow of breathable gas based on a determination whether a subject has completed an exhalation and/or based on the volume of gas delivered over time.

2. Description of the Related Art

Some types of respiratory therapy involve the delivery of a pressurized flow of breathable gas to the airway of a subject, e.g. using a mechanical ventilator. A therapy session may (be intended to) span eight or more hours, and may (be intended to) coincide and/or overlap, at least in part, with a subject's daily and/or nightly sleeping period. Some subjects treated with a mechanical ventilator may experience expiratory flow reduction, for example due to issues stemming from lower airway abnormalities such as chronic asthma, cystic fibrosis, or constrictive bronchiolitis.

SUMMARY OF THE INVENTION

Accordingly, one or more embodiments of the present disclosure provide a system that includes a pressure generator, one or more sensors, and one or more physical processors. The pressure generator is configured to provide a pressurized flow of breathable gas at a pressure level to an airway of a subject. The one or more sensors are configured to generate output signals conveying information related to breathing of the subject. The one or more physical processors are configured to determine one or more phase timing parameters related to the breathing of the subject based on the generated output signals; determine one or more breathing parameters of the subject based on the generated output signals, wherein the one or more breathing parameters indicate one or more of lung volume, tidal volume, and/or flow rate of the breathing of the subject; determine, during exhalations, whether the subject has completed an exhalation based on the one or more breathing parameters; and control the pressurized flow in accordance with the respiratory therapy regimen such that the pressure level of the pressurized flow corresponds to an inspiratory positive airway pressure (IPAP) level during inhalations and to an expiratory positive airway pressure (EPAP) level during exhalations, wherein control is based on the one or more phase timing parameters and the determination whether the subject has completed the particular exhalation.

It is yet another aspect of one or more embodiments of the present disclosure to provide a method to provide respiratory therapy to a subject. The method is implemented using a pressure generator, one or more sensors, and one or more physical processors. The method includes providing a pressurized flow of breathable gas at a pressure level to an airway of the subject; generating output signals conveying information related to breathing of the subject, wherein the breathing includes inhalations and exhalations; determining one or more phase timing parameters related to the breathing of the subject based on the generated output signals; determining one or more breathing parameters of the subject based on the generated output signals, wherein the one or more breathing parameters indicate one or more of lung volume, tidal volume, and/or flow rate of the breathing of the subject; determining, during exhalations, whether the subject has completed an exhalation based on the one or more breathing parameters; and controlling the pressurized flow of breathable gas in accordance with the respiratory therapy regimen such that the pressure level of the pressurized flow corresponds to an inspiratory positive airway pressure (IPAP) level during inspirations and to an expiratory positive airway pressure (EPAP) level during expirations, wherein the controlling is based on a) the one or more phase timing parameters, b) the determination whether the subject has completed the particular exhalation, or c) both a) and b).

It is yet another aspect of one or more embodiments to provide a system configured to provide respiratory therapy to a subject. The system includes means for providing a pressurized flow of breathable gas at a pressure level to an airway of the subject; means for generating output signals conveying information related to breathing of the subject, wherein the breathing includes inhalations and exhalations; means for determining one or more phase timing parameters related to the breathing of the subject based on the generated output signals; means for determining one or more breathing parameters of the subject based on the generated output signals, wherein the one or more breathing parameters indicate one or more of lung volume, tidal volume, and/or flow rate of the breathing of the subject; means for determining whether, during exhalations, the subject has completed an exhalation based on the one or more breathing parameters; and means for controlling the pressurized flow of breathable gas in accordance with the respiratory therapy regimen such that the pressure level of the pressurized flow corresponds to an inspiratory positive airway pressure (IPAP) level during inspirations and to an expiratory positive airway pressure (EPAP) level during expirations, wherein operation of the means for controlling is based on a) the one or more phase timing parameters, b) the determination whether the subject has completed the particular exhalation, or c) both a) and b).

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Subjects using respiratory therapy, in particular mechanical ventilation, may have trouble exhaling completely before the subsequent inhalation starts. Incomplete exhalation may add to a subject's discomfort and may have medical consequences, including but not limited to hypercapnia, air trapping, hyperinflation, and/or other conditions. By virtue of this disclosure, one or more parameters of the respiration of a subject may be maintained at a target level, above or below a target threshold as appropriate, or generally controlled in a way to reduce hypercapnia while providing respiratory therapy.

Figure 1:
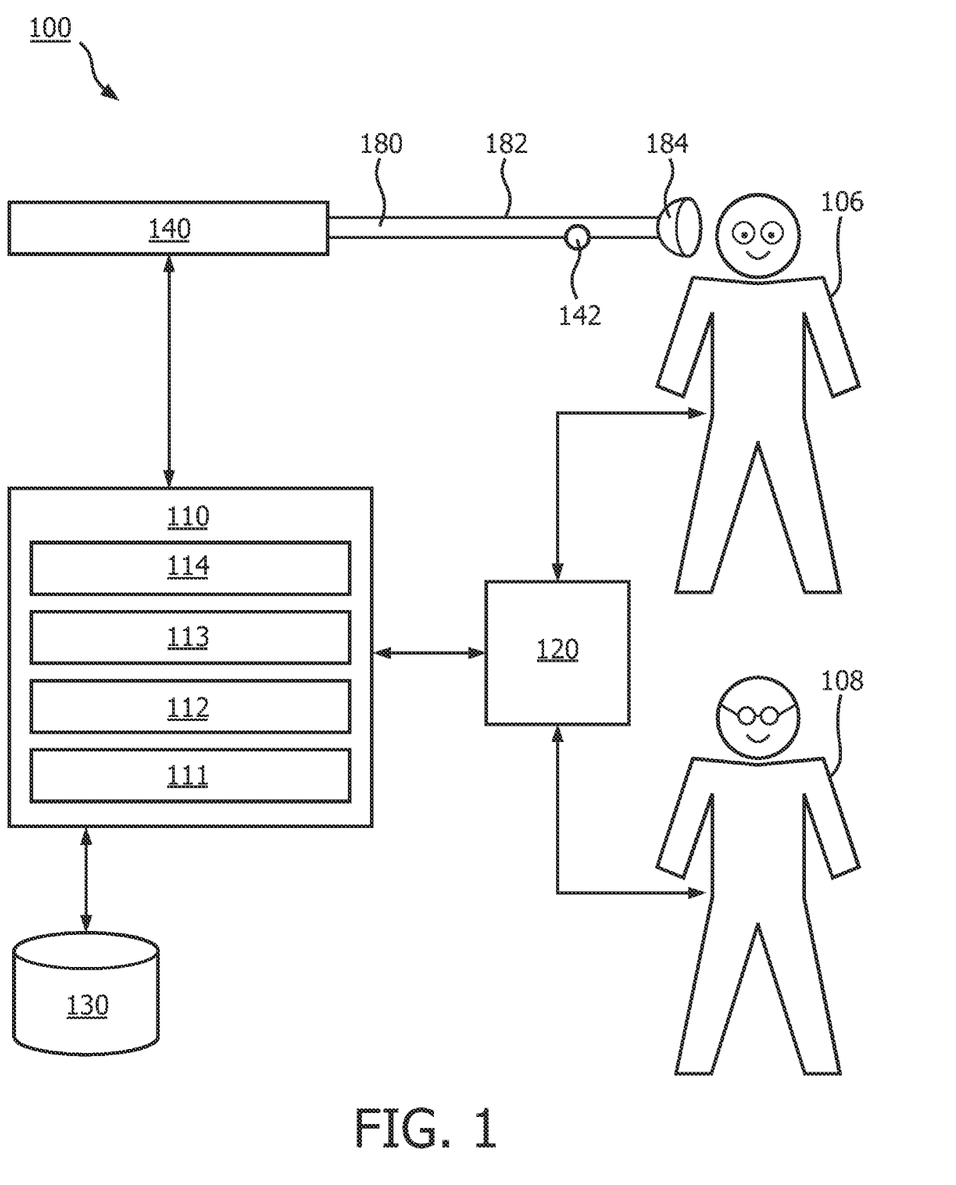
FIG. 1 schematically illustrates a system to provide respiratory therapy to a subject, according to certain embodiments.

FIG. 1 schematically illustrates a system 100 configured to provide respiratory therapy to subjects, for example a subject 106 having an airway. System 100 may be implemented as, integrated with, and/or operating in conjunction with a respiratory device that provides a pressurized flow of breathable gas along a flow path to subject 106. System 100 may include one or more of a pressure generator 140, a subject interface 180, one or more sensors 142, an electronic storage 130, a user interface 120, a processor 110, a therapy component 111, a parameter determination component 112, a completion component 113, a control component 114, and/or other components. System 100 may be configured to provide respiratory therapy to subject 106.

Pressure generator 140 of system 100 in FIG. 1 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via one or more subject interfaces 180. Subject interface 180 may sometimes be referred to as a delivery circuit.

As depicted in FIG. 1, pressure generator 140 fluidly communicates with subject interface 180. Subject interface 180 fluidly communicates, via a subject interface appliance 184, with the airway of subject 106. The configuration of various components in FIG. 1 is not intended to limit the scope of the described technology in any way. For example, in some embodiments, system 100 may include a humidifier and/or interface heating system disposed between pressure generator 140 and subject 106.

Respiratory therapy may be implemented as pressure control, pressure support, volume control, and/or other types of support and/or control. For example, to support inspiration, the pressure of the pressurized flow of breathable gas may be adjusted to an inspiratory positive airway pressure (interchangeably referred to as inspiratory pressure, IPAP, or IPAP level). This mode of operation may be referred to as the inspiratory mode of operation or the inhalation mode of operation. To support expiration, the pressure and/or flow of the pressurized flow of breathable gas may be adjusted to an expiratory positive airway pressure (interchangeably referred to as expiratory pressure, EPAP, or EPAP level). This mode of operation may be referred to as the expiratory mode of operation or the exhalation mode of operation. Other schemes for providing respiratory support and/or ventilation through the delivery of the pressurized flow of breathable gas are contemplated. Subject 106 may but need not initiate one or more phases of respiration. Devices that provide different IPAP and EPAP levels may be referred to as dual (positive) airway pressure devices. An example of a dual positive airway pressure device is a BiPAP® device.

System 100 may be configured to adjust and/or maintain levels of pressure, flow, humidity, velocity, acceleration, and/or other parameters of the humidified, pressurized flow of breathable gas. One or more adjustments may occur in substantial synchronization with the breathing cycle of the subject. In some embodiments, one or more operating levels (e.g. pressure, volume, etc.) are adjusted on a relatively ongoing manner (e.g., each breath, every few breaths, every few seconds, etc.) during an individual session of respiratory therapy to titrate and/or control the therapy. Alternatively, and/or simultaneously, adjustments to one or more operating levels of system 100 and/or any component thereof may be made more intermittently and/or between therapy sessions rather than during a particular therapy session.

Pressure generator 140 is configured to provide and/or deliver a pressurized flow of breathable gas to the airway of subject 106, e.g. via one or more subject interfaces 180. Subject interface 180 may include a conduit 182 and/or a subject interface appliance 184. As depicted in FIG. 1, subject interface 180 may include a conduit 182. Conduit 182 may include a flexible length of hose, or other conduit. As depicted in FIG. 1, conduit 182 may place subject interface appliance 184 in fluid communication with pressure generator 140. Conduit 182 may form a flow path through which the pressurized flow of breathable gas is communicated between subject interface appliance 184 and pressure generator 140.

Subject interface appliance 184 of system 100 in FIG. 1 is configured to deliver the pressurized flow of breathable gas to subject 106, e.g. to the airway of subject 106. Subject interface appliance 184 may be configured to be removably coupled to conduit 182. Subject interface appliance 184 may be configured to be installed in the face of subject 106 to place the airway of subject 106 in fluid communication with conduit 182 for delivery of a pressurized flow of breathable gas through conduit 182 to the airway of subject 106.

In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface. Subject interface appliance 184 may include any appliance suitable for the described function.

Electronic storage 130 of system 100 in FIG. 1 comprises physical electronic storage media that electronically stores information, e.g. digital information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas and/or respiratory parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., a user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing operational settings of pressure generator 140 as selected and/or preferred by subject 106. An example of information that user 108 or subject 106 may provide to system 100 is a target temperature or target pressure level during respiratory therapy. Examples of interface devices suitable for inclusion in user interface 120 include a keypad, buttons, switches, a keyboard, knobs, dials, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the embodiment of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying information related to the breathing of subject 106 and/or to physiological parameters of subject 106, including but not limited to respiratory parameters. The breathing of subject 106 may include breathing phases. Individual breaths include an inhalation phase, and exhalation phase, and zero, one, or two respiratory pauses. For example, a first respiratory pause may be defined between an inhalation phase and a subsequent exhalation phase. Alternatively, and/or simultaneously, a second respiratory pause may be defined between an exhalation phase and a subsequent inhalation phase. Transitions between respiratory phases and/or respiratory pauses may be determined based on one or more respiratory parameters, including but not limited to one or more flow rate parameters. Transitions between respiratory phases and/or respiratory pauses may correspond to transitions between different modes of operation. In some embodiments, onset of an inhalation phase may correspond to a flow rate in a particular direction (into the airway of the subject), whereas onset of an exhalation phase may correspond to a flow rate in the opposite direction (out of the airway of the subject). In some embodiments, respiratory pauses may correspond to either no flow rate in any direction, or a flow rate below a minimum flow rate threshold.

One or more sensors 142 may be in fluid communication with conduit 182, subject interface appliance 184, and/or other components of system 100. In some embodiments, the generated output signals may convey measurements related to parameters of the flow of breathable gas within system 100. By way of non-limiting example, the parameters may include respiratory parameters, phase timing parameters, breathing parameters, physiological parameters, environmental parameters, medical parameters, and/or other parameters.

The parameters may include one or more of (peak) flow, flow rate, volume, leak flow, leak volume, (airway) pressure, barometric pressure, temperature, humidity, velocity, acceleration, and/or other parameters. The respiratory parameters may include phase timing parameters, including but not limited to parameters related to breathing phases, transitions in breathing between inhalations and exhalations, transition time from peak inhalation flow rate to peak exhalation flow rate and/or vice versa, transitions moments or durations, breathing period, respiratory rate, inspiratory period, expiratory period, start and/or end in inspiratory phases, start and/or end of expiratory phases, transition rates and/or slopes, and/or other respiratory timing parameters, including derivatives and/or combinations thereof.

Environmental parameters may be related to one or more of the parameters of electromagnetic radiation, various temperatures, humidity levels, and/or other environmental parameters, which may be related to environmental conditions near system 10 or near subject 106. One or more medical parameters may be related to monitored vital signs of subject 106, physiological parameters of subject 106, and/or other medical parameters of subject 106.

One or more sensors 142 may generate output signals conveying information related to parameters associated with the state and/or condition of an airway of subject 106, the breathing of subject 106, the breathing rate of subject 106, the gas delivered to subject 106, the composition, temperature, and/or humidity of the gas delivered to subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from one or more sensors 142 may be transmitted to processor 110, user interface 120, electronic storage 130, and/or other components of system 100. This transmission may be wired and/or wireless.

Physiological parameters may be related to patient movement, cardio-vascular function, pulmonary function, central nervous system function, local motor-neuron function, mechanical motion of the body or its organs, and/or other parameters. In some embodiments, sensor 142 may include sensors to monitor subject 106, including, but not limited to, sensors to measure polysomnography, electro-encephalography (EEG), electro-oculography (EOG), electromyography (EMG), electrocardiography (ECG), and/or sensors for other types of monitoring.

The illustration of sensor 142 including one member in FIG. 1 is not intended to be limiting. The illustration of a sensor 142 at or near subject interface appliance 184 is not intended to be limiting, though that position/location may be preferred in some embodiments to provide feedback and/or information regarding one or more current flow rates of the breathing of the subject and/or of the pressurized flow of breathable gas being delivered to the airway of subject 106. For example, a current flow rate may function as feedback for a target flow rate for controlling pressure generator 140.

Processor 110 of system 100 in FIG. 1 is configured to provide information processing capabilities in system 100. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program components. The one or more computer program components include one or more of therapy component 111, parameter determination component 112, completion component 113, control component 114, and/or other components. Processor 110 may be configured to execute components 111-114 by software; hardware; firmware; some combination of software, hardware, and/or firmware; and/or other mechanisms for configuring processing capabilities on processor 110.

It should be appreciated that although components 111-114 are illustrated in FIG. 1 as being co-located within a single processing unit, in embodiments in which processor 110 includes multiple processing units, one or more of components 111-114 may be located remotely from the other components. The description of the functionality provided by the different components 111-114 described herein is for illustrative purposes, and is not intended to be limiting, as any of components 111-114 may provide more or less functionality than is described. For example, one or more of components 111-114 may be eliminated, and some or all of its functionality may be provided by other ones of components 111-114. Note that processor 110 may be configured to execute one or more additional components that may perform some or all of the functionality attributed below to one of components 111-114. In some embodiments, some or all of the described functionality of an individual computer program component may be incorporated, shared, embedded, and/or integrated into one or more other computer program components or elsewhere within system 100.

Therapy component 111 may be configured to obtain a respiratory therapy regimen for subject 106. For example, the obtained respiratory therapy regimen may be a recommended respiratory therapy regimen. In some embodiments, therapy component 111 may be configured to obtain a respiratory therapy regimen from a user (such as subject 106 and/or user 108, a caregiver, a therapy decision-maker, etc.). In some embodiments, therapy component 111 may be configured to obtain and/or receive a respiratory therapy regimen that may be determined and/or devised algorithmically based on, at least, subject-specific information. A respiratory therapy regimen may specify system operation for multiple different modes of operation, including but not limited to inhalation and exhalation modes of operation. In some embodiments, therapy component 111 may be configured to determine a respiratory therapy regimen, e.g. based on, at least, subject-specific information. Additional information that may be used to determine a respiratory therapy regimen may be obtained from and/or through a knowledge base (or knowledge database).

In some embodiments, the obtained respiratory therapy regimen may include an inspiratory positive airway pressure (IPAP) level, an expiratory positive airway pressure (EPAP) level, and/or other recommended pressure levels. A respiratory therapy regimen may include a (target) respiratory rate, a (target) respiratory volume, a (target) minute volume, a (target) volumetric rate of expulsion of $CO_2$, and/other respiratory parameters. As used herein, a target minute volume need not be restricted to a volume of gas inhaled or exhaled per minute, but may refer to a volume of gas inhaled or exhaled per unit of time. In some embodiments, the pressure levels may be determined and/or selected to maintain breathing by subject 106 that is free of apneas, hypopneas, and/or other respiratory events, or at least expected to be so. In some embodiments, the pressure levels may be determined and/or selected such that the airway of subject 106 is deemed and/or expected to be stable and/or unobstructed. In some embodiments, the pressure levels may be selected to be below a prescribed continuous positive airway pressure (CPAP) level to treat apnea and/or other respiratory events. In some embodiments, a target included in a respiratory therapy regimen may be adjusted during therapy, e.g. based on measurements and/or feedback obtained from output signals generated by one or more sensors 142.

Determinations and/or selections by therapy component 111 may be based on determinations by other computer program components.

In some embodiments, a respiratory therapy regimen may include, define, and/or otherwise correspond to triggers that indicate that system 100 should transition from one mode of operation to another mode of operation. For example, a particular target respiratory rate may correspond to time-out triggers (also referred to as timed triggers, e.g. an inspiratory timed trigger or an expiratory timed trigger) that indicate a particular amount of time has passed since the onset of a particular breathing phase. To maintain the target respiratory rate, the mode of operation needs to transition to the subsequent breathing phase after a time-out trigger has occurred. however, maintaining the target respiratory rate may be a lower priority than, e.g., completing an exhalation fully, exhalation as much gas as a subject is able to exhale, and/or another respiratory achievement that may be desired for the subject.

Figure 3:
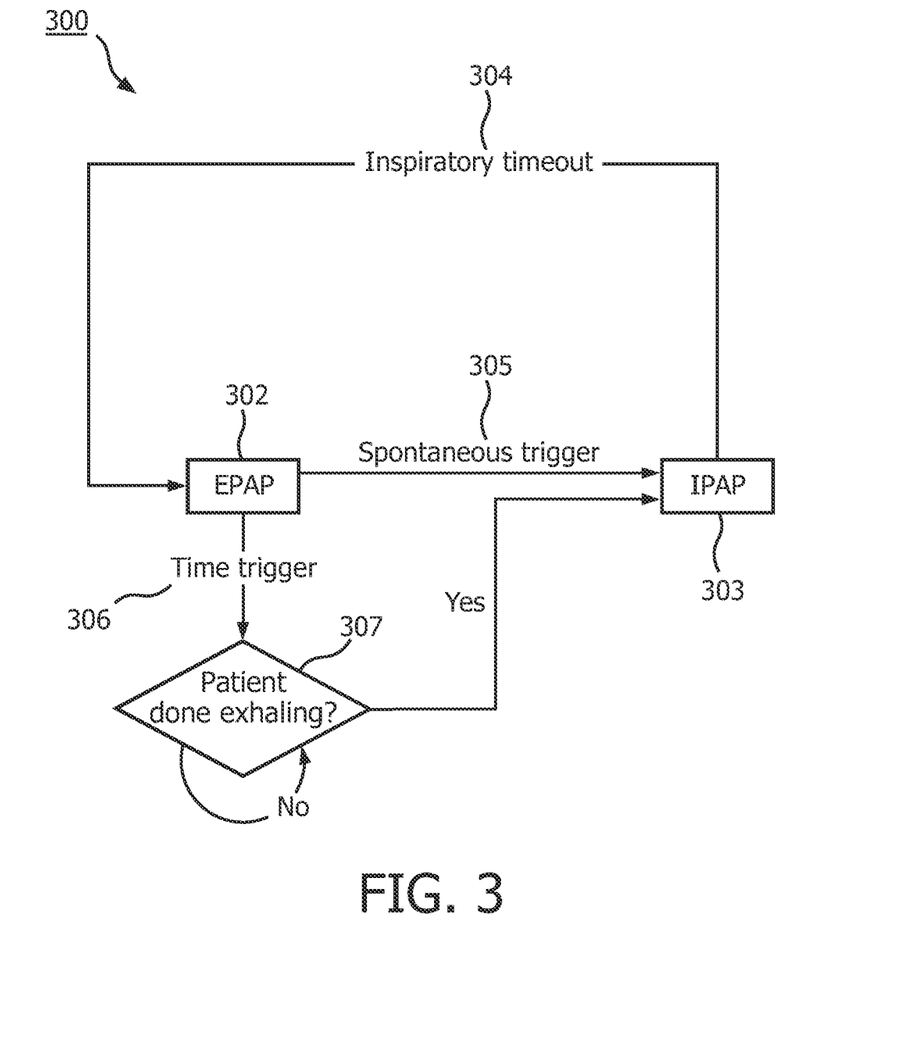
FIG. 3 illustrates a control chart for a system to provide respiratory support that alternates between an inspiratory mode of operation and an expiratory mode of operation, in accordance with one or more embodiments.

By way of illustration, FIG. 3 illustrates a control chart 300 for a system (similar to or the same as system 100 in FIG. 1) to provide respiratory support that alternates between an inspiratory mode of operation and an expiratory mode of operation. The expiratory mode of operation is indicated by label "EPAP 302". The inspiratory mode of operation is indicated by label "IPAP 303". Control of the system transitions from the inspiratory mode of operation to the expiratory mode of operation (i.e. from IPAP 303 to EPAP 302) responsive to the event and/or condition labeled "Inspiratory Timeout 304," which is covered in more detail in FIG. 4. Control of the system transitions from the expiratory mode of operation to the inspiratory mode of operation (i.e. from EPAP 302 to IPAP 303) responsive to one of two events and/or conditions, labeled "Spontaneous Trigger 305" and "Timed Trigger 306" respectively. The event labeled "Spontaneous Trigger 305" corresponds to a spontaneous subject-initiated effort that indicates the onset of an inhalation. In other words, if a subject starts to take a breath (and/or makes an effort to do so) the system may transition accordingly in order to support the subject's breathing.

The event labeled "Timed Trigger 306" corresponds to a system-generated trigger, based on e.g. a target respiratory rate, that indicates the system is ready to transition to the inspiratory mode of operation. However, before such a transition occurs, a system as controlled by control chart 300 may verify whether the subject has completed the current exhalation, which is indicated by label "Patient Done Exhaling? 307". A determination that a subject has completed an exhalation may be made by a completion component similar to or the same as completion component 113 (FIG. 1). Upon such a verification, the system may transition to the inspiratory mode of operation.

Parameter determination component 112 may be configured to determine one or more phase timing parameters related to the breathing of subject 106, including but not limited to respiratory timing parameters described elsewhere in this disclosure. Determination by parameter determination component 112 may be based on output signals generated by one or more sensors 142 and/or determinations by other computer program modules. For example, one or more phase timing parameters may be related to one or more breathing phases of subject 106. For example, phase timing parameters may include the moment of onset of an inhalation, the moment of onset of an exhalation, (estimated or measured) duration or period of inhalation, (estimated or measured) duration or period of exhalation, inspiratory period, inspiratory pressure, pressure support (difference between expiratory and inspiratory pressure), expiratory period, pause between inhalation and exhalation and/or vice versa, transition time from peak inhalation flow rate to peak exhalation flow rate and/or vice versa, start and/or end of inhalation phases, start and/or end of exhalation phases, transition rates and/or slopes, and/or other respiratory timing parameters, combinations of respiratory timing parameters, and/or parameters based thereon. In some embodiments, a phase timing parameter may include, for an individual inhalation phase, the moment when the flow rate and/or the volume inhaled breaches a minimum flow rate and/or volume threshold. In some embodiments, a phase timing parameter may include, for an individual exhalation phase, the moment when the flow rate and/or the volume exhaled breaches a minimum flow rate and/or volume threshold.

Parameter determination component 112 may be configured to determine one or more breathing parameters of subject 106. As used herein, breathing parameters may include gas parameters. By way of non-limiting example, breathing parameters may include one or more of (peak) flow, flow rate, leak flow, leak correction volume, (estimated) flow limitation during exhalation, residual volume, maximum inspiratory flow per breath, (tidal) volume, minute volume, inhalation or exhalation pressures, respiratory rate, breathing period, inhalation time or period, exhalation time or period, respiration flow curve shape, transition time from inhalation to exhalation and/or vice versa, respiration pressure curve shape, maximum proximal pressure drop (per breathing cycle and/or phase), change in pressure during the first 0.1 s (or another amount of time) of an inspiration, change in flow rate during the last 0.1 s (or another amount of time) of an exhalation, (estimated) airway resistance, (estimated) airway compliance, gas temperature, gas humidity, gas velocity, gas acceleration, gas composition (e.g. concentration(s) of one or more constituents such as, e.g., $CO_2$), thermal energy dissipated, (intentional) gas leak, and/or other measurements related to the (pressurized) flow of breathable gas and/or other breathing parameters.

In some embodiments, a breathing parameter may indicate, correspond to, and/or be derived from any of the parameters mentioned herein, for example by virtue of a previously known and/or calibrated mathematical relationship. In some embodiments, a breathing parameter may include ratios and/or other combinations of multiple other parameters. Some or all of this functionality may be incorporated, shared, and/or integrated into other computer program components in system 100.

Completion component 113 may be configured to determine whether subject 106 has completed a particular inhalation or exhalation. During inhalations, completion module 113 may be configured to determine whether and/or when subject 106 has completed an inhalation. During exhalations, completion module 113 may be configured to determine whether and/or when subject 106 has completed an exhalation. Determinations by completion module 113 may be based on output signals generated by one or more sensors 142 and/or determinations by other computer program modules. For example, a determination that subject 106 has completed a particular exhalation may be based on the value of the flow rate of the exhalation of subject 106. For example, a flow rate of zero (or a value sufficiently close to zero, below a threshold flow rate) may indicate an exhalation has been completed. Alternatively, and/or simultaneously, a determination that subject 106 has completed a particular exhalation may be based on one or more measurements of residual lung volume. For example, a first residual lung volume of breathable gas being delivered to the airway of subject 106 may be measured or estimated, and a second residual lung volume of the subsequent exhalation may be subtracted from the first residual lung volume to determine that the lung volume is sufficiently close to the functional residual or quiet volume of the patient's respiratory cycle or that all inhaled tidal volume has been exhaled.

Logical combinations of a flow-rate-based determination and a volume-based determination are also envisioned within the scope of this disclosure. The term "volume-based" may include approaches using either lung volume, tidal volume, or both. In some embodiments, completion component 113 may be configured to determine whether a subject has completed a particular inhalation, e.g. based on knowledge gathered about previous inhalations, in combination with one or more parameters indicating one or more of a lung volume, tidal volume, and/or a flow rate of the breathing of subject 106 and/or the delivered pressurized flow of breathable gas.

Control component 114 may be configured to control operation of system 100, pressure generator 140, and/or related components. Control component 114 may be configured to perform control functionality in multiple modes of operation. Control component 114 may be configured to control transitions between different modes of operation. Control component 114 may be configured to determine what the current mode of operation is, and/or share such information with other components of system 100. Control component 114 may be configured to control pressure generator 140 such that one or more gas parameters of the pressurized flow of breathable gas are adjusted and/or varied over time, e.g. in accordance with a respiratory therapy regimen. Control component 114 may be configured to control pressure generator 140 to provide the pressurized flow of breathable gas at inhalation pressure levels (e.g. an IPAP level that is included in a respiratory therapy regimen) during inhalation phases, and at exhalation pressure levels (e.g. an EPAP level that is included in a respiratory therapy regimen) during exhalation phases.

Parameters determined by other computer program components and/or received through one or more sensors 142 may be used by control component 114, e.g. in a feedback manner, to adjust one or more therapy modes/settings/operations of system 100. Alternatively, and/or simultaneously, signals and/or information received through user interface 120 may be used by control component 114, e.g. in a feedback manner, to adjust one or more therapy modes/settings/operations of system 100. Control component 114 may be configured to time its operations relative to the transitional moments in the breathing cycle of a subject, one or more phase timing parameters, over multiple breath cycles, and/or in any other relation to any detected occurrences or determinations by parameter determination component 112.

In some embodiments, control component 114 may be configured to control a transition from a particular exhalation to a subsequent inhalation based on the determination whether subject 106 has completed the particular exhalation. By way of non-limiting example, FIG. 3 illustrates an example of controlling transitions between different modes of operation. In some embodiments, control component 114 may be configured to control a transition from a particular inhalation to a subsequent exhalation based on the determination whether subject 106 has completed the particular inhalation, whether a timed trigger has occurred, whether the inspiratory period has passed, and/or other conditions. In FIG. 3, such a transition occurs responsive to the even and/or condition labeled "Inspiratory Timeout 304".

Figure 4:
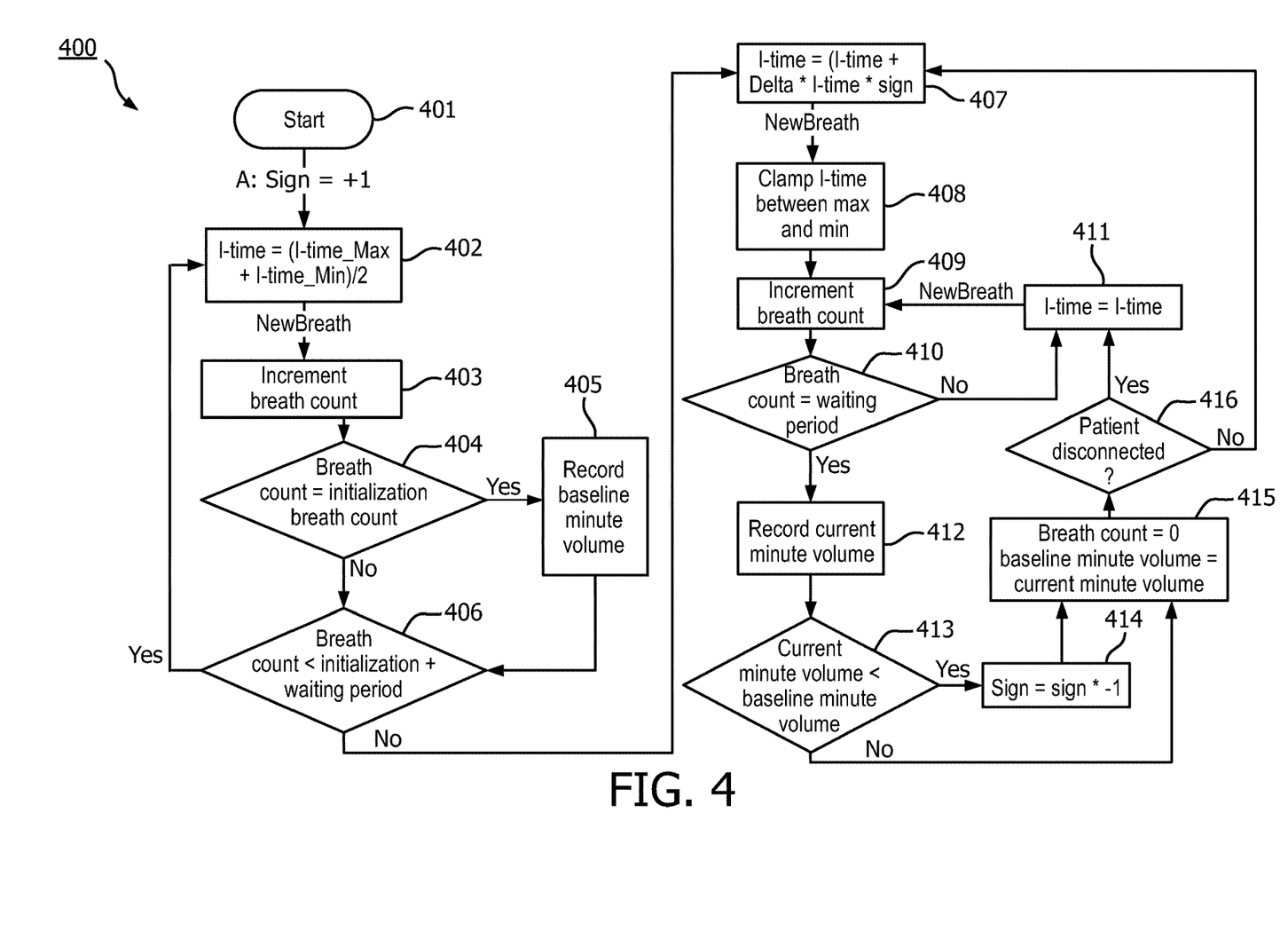
FIG. 4 illustrates a control chart for a system to provide respiratory support that determines one or more parameters related to inhalations, in accordance with one or more embodiments.

By way of illustration, FIG. 4 illustrates a control chart 400 for a system (similar to or the same as system 100 in FIG. 1) to provide respiratory support that alternates between an inspiratory mode of operation and an expiratory mode of operation, wherein transitions from an inspiratory mode to an expiratory mode are based on an inspiratory period "I-time" having passed since, e.g., the onset of a particular inhalation. Other definitions of inspiratory period as commonly used in mechanical ventilators may be used herein. For example, inspiratory period may be determined based on, at least in part, one or more preceding respiratory cycles, and in particular one or more phase timing parameters for one or more preceding inspiratory phases. Responsive to I-time having passed, system 100 may transition from an inspiratory mode of operation to an expiratory mode of operation.

As depicted in FIG. 4, operation of a system may start at step 401, which transitions to step 402 while initializing variable "Sign" to the value 1. At step 402, inspiratory period "I-time" may be initialized to a particular value, for example half of the sum of the highest and lowest available settings for I-time. Step 402 transitions to step 403 while providing the subject with a respiratory cycle, as indicated by the label "NewBreath" between steps 402 and 403. At step 403, a breath counter, also referred to as a respiration counter, is incremented. Step 403 transitions to step 404. At step 404, a predetermined variable indicating a number of breaths, called "initialization breath count," is compared to the breath counter. If the values match, step 404 transitions to step 405. Else, step 404 transitions to step 406. At step 406, the breath counter is tested against a predetermined initialization value plus a waiting period (which is indicated by a number of breaths). If the breath counter is found to be lower, step 406 transitions to step 402, else it transitions to step 407.

At step 405, a baseline minute volume is recorded. Step 405 transitions to step 406. At step 407, the value of I-time is adjusted by a fraction "Delta". The parameter that is adjusted, in this case I-time, may be referred to as a control parameter. The control parameter is adjusted in order to optimize a patient parameter, in this case minute volume. The value of the variable "Sign" determines whether the value of I-time is increased or decreased at this step. Step 407 transitions to step 408 while providing the subject with a respiratory cycle, as indicated by the label "NewBreath" between steps 407 and 408. At step 408, the value of I-time is tested against predetermined maximum and minimum I-time values as a precaution against the value becoming too high or too low. Step 408 transitions to step 409. At step 409, the breath counter is incremented. Step 409 transitions to step 410. At step 410, the breath counter is tested against the predetermined waiting period (which is indicated by a number of breaths). If the values match, step 410 transitions to step 412. Else, step 410 transitions to step 411. At step 412, a current minute volume is recorded. Step 412 transitions to step 413. At step 413, the current minute volume is tested against the baseline minute volume. If the current minute volume is found to be lower, step 413 transitions to step 414, else it transitions to step 415.

At step 414, the value of the variable "Sign" is inverted. Step 414 transitions to step 415. At step 415, the breath counter is reset to value zero, and the baseline minute volume is set to the most recently recorded current minute volume from step 412. Step 415 transitions to step 416. At step 416, the system tests whether the patient is disconnected or not from the system. If so, step 416 transitions to step 411. Else, step 416 transitions to step 407. Step 411 transitions to step 409 while providing the subject with a respiratory cycle, as indicated by the label "NewBreath" between steps 411 and 409. The steps between 401 and 406 may be regarded as initialization steps. After initialization, control chart 400 operates between steps 407 up to 416. The value of inspiratory period "I-time" is increased gradually as long as the current minute volume keeps being higher than the previous recorded minute volume. As soon as the minute volume fails to be higher, the value of inspiratory period "I-time" is gradually decreased until the current minute volume is once again higher than the previous recorded minute volume. In other words, control chart 400 operates to increase the inspiratory period so long as such increases correspond to an increase in minute volume.

In the scenario exemplified by control chart 400 in FIG. 4, the patient parameter to be optimized is minute volume, which directly corresponds to the metabolic expulsion of Carbon Dioxide, and the control parameter was I-time. However, it is envisioned within the scope of this disclosure that the minute volume may be replaced by end-tidal $CO_2$ ($EtCO_2$), transcutaneous $CO_2$ ($TcCO_2$), arterial blood gas measurements, and/or any other breathing parameters that indicate hypercapnia, as well as combinations and derivatives thereof. Alternatively, and/or simultaneously, the control parameter—in this case I-time—may be replaced by Peak Flow, Pressure Support, Pressure, Flow Shape, and/or other parameters upon which control of the pressurized flow of breathable gas may be based, provided that the control parameter affects the metabolic expulsion of $CO_2$ in an understood way. In the broader scope, a control parameter may be controlled and/or adjusted in alternative directions (i.e. up or down) until there is an indication of a decrease in $CO_2$ expulsion. At that point, the direction of adjustment may be reversed. The use of minute volume and I-time is exemplary and not intended to be limiting in any way. In some embodiments, Pressure Support may be used as a control parameter. In some embodiments, an adjustment algorithm may change both Pressure Support and I-time together in an organized manner.

Figure 5:
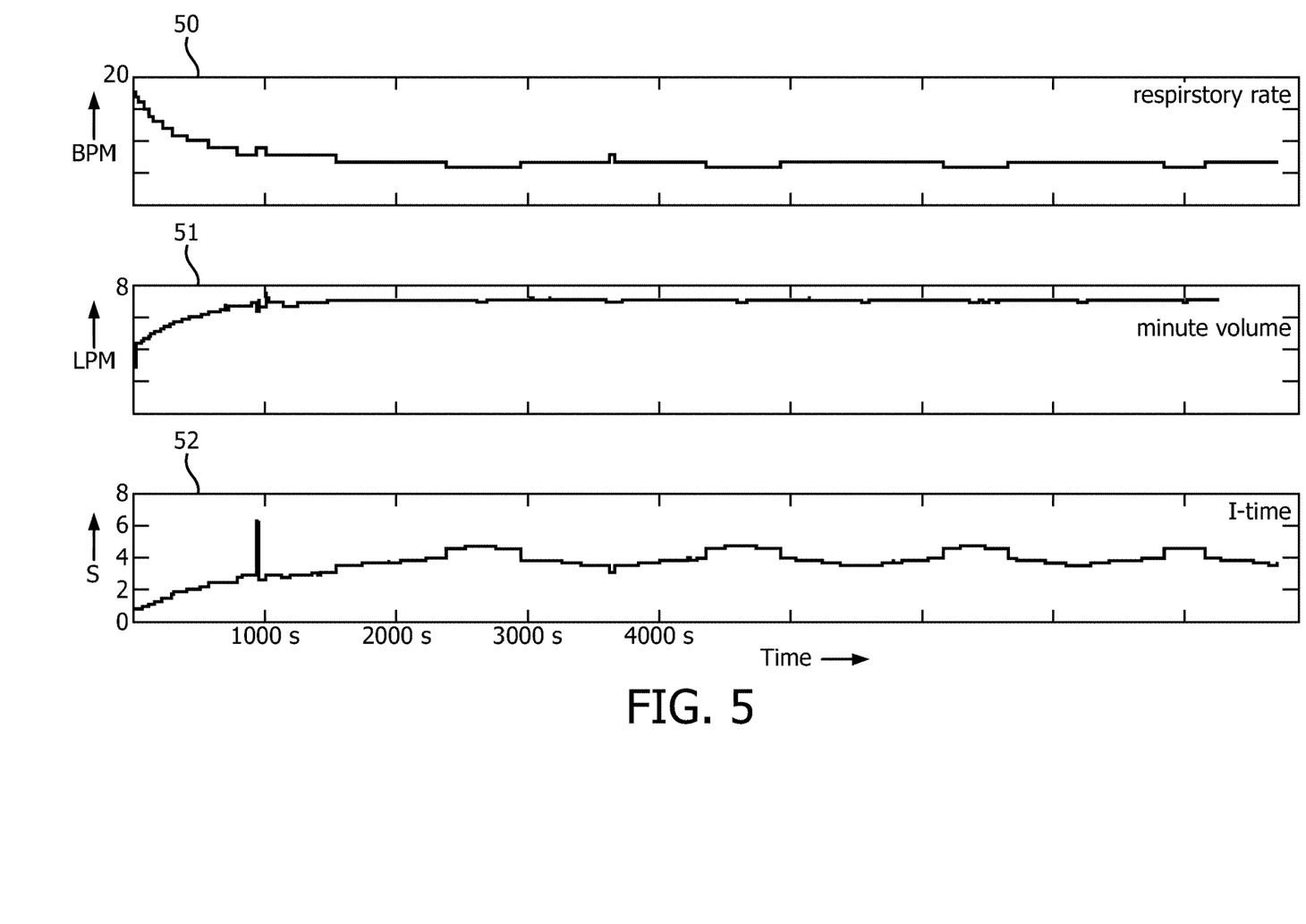
FIG. 5 illustrates three charts of exemplary respiration of a subject using the systems and methods described herein.

By way of illustration, FIG. 5 illustrates three charts of exemplary respiration of a subject as controlled according to control chart 300 (FIG. 3) and control chart 400 (FIG. 4). FIG. 5 depicts a respiratory rate 50 (measured in breaths per minute, or BPM), a minute volume 51 (measured in liters per minute, or LPM), and an inspiratory period 52 (or "I-time") as measured in seconds. The horizontal axis depicts time passing, spanning a total of 10000 seconds. In the first 1000 seconds, respiratory rate 50 starts relatively high, but is gradually reduced. At the same time, minute volume 51 starts relatively low, but is gradually increased. At the same time, inspiratory period 52 starts relatively low, but is gradually increased. In the second 1000 seconds, respiratory rate 50 is further reduced, inspiratory period 52 is further increased, and minute volume 51 is maintained at a relatively high level.

The time between about 2000 seconds and about 4000 seconds illustrates a pattern of behavior that repeats about three times in FIG. 5. During this time, the system attempts to increase the inspiratory period 52 even more. However, since the corresponding minute volume 51 is reduced as well (e.g. around about 2600 seconds), the system reverses course and reduces inspiratory period 52. Inspiratory period 52 is reduced until, around 3700 seconds, the corresponding minute volume 51 once again is increased compared to a previous measurement. Note that periods of increased inspiratory period 52 (e.g. between about 2400 seconds and about 3000 seconds) correspond with a similar period of decreased respiratory rate 50, as depicted about four times between about 2000 seconds and about 10000 seconds. Note that, for the period up to about 3000 seconds, respiratory rate 50 is gradually reduced while, at the same time, minute volume 51 gradually increases.

In some embodiments, the one or more breathing parameters determined by parameter determination component 112 may indicate a volumetric rate of expulsion of $CO_2$. Such a volumetric rate may be measured and/or determined for a set of one or more breathing cycles. In some embodiments, a volumetric rate of expulsion of $CO_2$ may be measured and/or determined for multiple sets of one or more breathing cycles, for example subsequent sets of breathing cycles. In some embodiments, control component 114 may be configured to adjust the (timing of the) pressurized flow of breathable gas delivered to the airway of subject 106 and/or one or more phase timing parameters (including but not limited to inspiratory period) to increase the volumetric rate of expulsion of $CO_2$.

Figure 2:
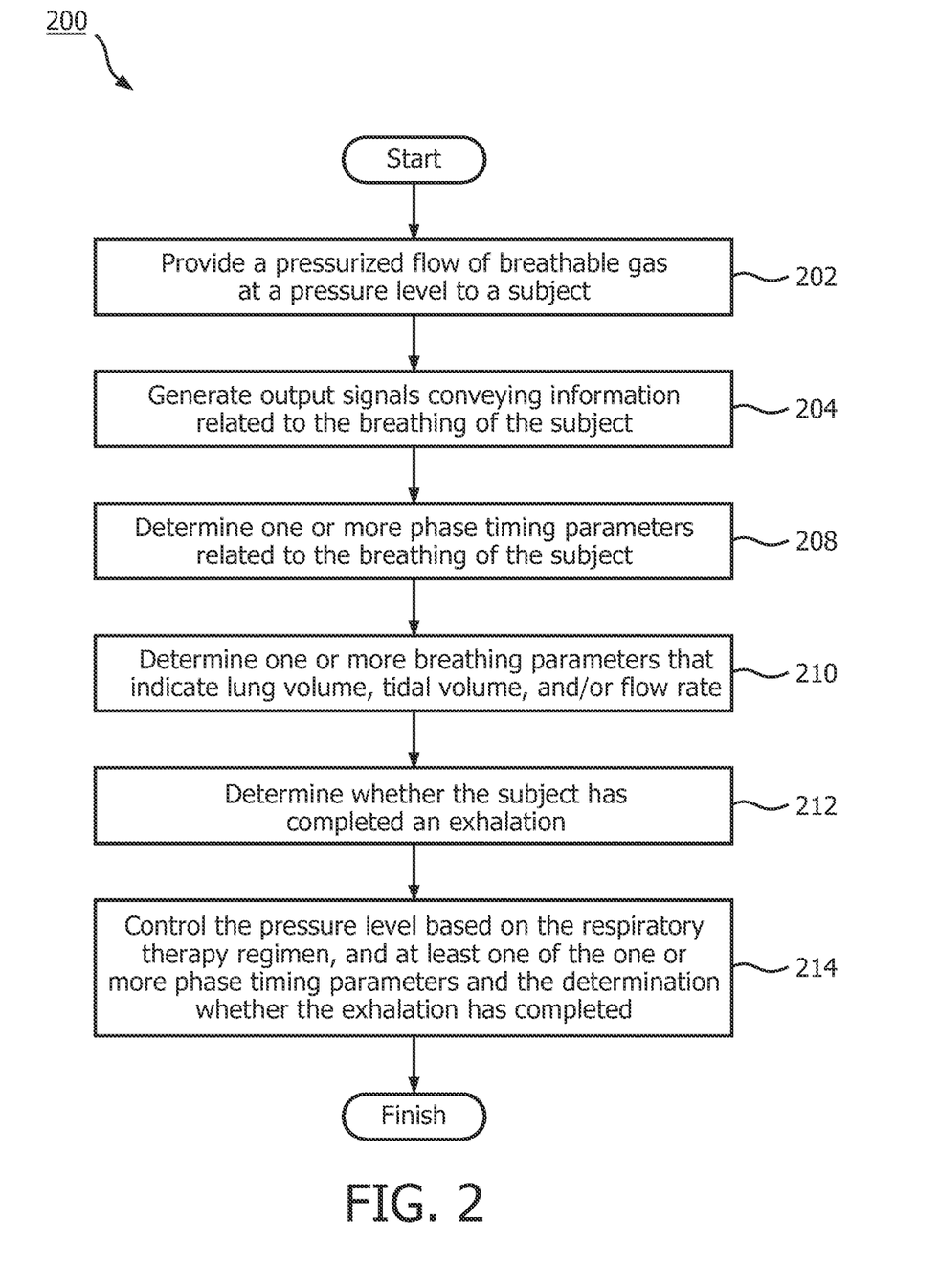
FIG. 2 illustrates a method to provide respiratory therapy to a subject, according to certain embodiments.

FIG. 2 illustrates a method 200 to provide respiratory therapy to a subject. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is provided at a pressure level to an airway of the subject. In some embodiments, operation 202 is performed by a pressure generator the same as or similar to pressure generator 140 (shown in FIG. 1 and described herein).

At an operation 204, output signals conveying information related to the breathing of the subject are generated. The breathing includes a breathing phase. The breathing includes inhalations and exhalations. In some embodiments, operation 204 is performed by one or more sensors the same as or similar to sensor 142 (shown in FIG. 1 and described herein).

At an operation 208, one or more phase timing parameters are determined that are related to the breathing of the subject based on the generated output signals. In some embodiments, operation 208 is performed by a parameter determination component the same as or similar to parameter determination component 112 (shown in FIG. 1 and described herein).

At an operation 210, one or more breathing parameters of the subject are determined based on the generated output signals. The one or more breathing parameters indicate one or more of lung volume, tidal volume, and/or flow rate of breathable gas delivered to the airway of the subject. In some embodiments, operation 210 is performed by a parameter determination component the same as or similar to parameter determination component 112 (shown in FIG. 1 and described herein).

At an operation 212, it is determined, during exhalations, whether the subject has completed an exhalation based on the one or more breathing parameters. In some embodiments, operation 212 is performed by a completion component the same as or similar to completion component 113 (shown in FIG. 1 and described herein).

At an operation 214, the pressurized flow of breathable gas is controlled in accordance with the respiratory therapy regimen such that the pressure level of the pressurized flow corresponds to the IPAP level during inspirations and to the EPAP level during expirations. Control is based on a) the one or more phase timing parameters, b) the determination whether the subject has completed the particular exhalation, or c) both a) and b). In some embodiments, operation 214 is performed by a control component the same as or similar to control component 114 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to provide mechanical ventilation to a subject, the system comprising:
   a pressure generator configured to provide a pressurized flow of breathable gas at a pressure level to an airway of a subject;
   one or more sensors configured to generate output signals conveying information related to breathing of the subject, wherein the breathing includes inhalations and exhalations; and
   one or more physical processors configured to:
      determine one or more phase timing parameters related to breathing phases of the subject based on the generated output signals, the one or more phase timing parameters comprising a moment and/or a duration related to the breathing phases;
      determine one or more breathing parameters of the subject based on the generated output signals, wherein the one or more breathing parameters indicate one or more of lung volume, tidal volume, and/or flow rate of the breathing of the subject;
      determine, during exhalations, whether the subject has completed a particular exhalation based on the one or more breathing parameters; and
      control the pressurized flow in accordance with a respiratory therapy regimen such that the pressure level of the pressurized flow corresponds to an inspiratory positive airway pressure level during the inhalations and to an expiratory positive airway pressure level during the exhalations; and
      adjust the pressurized flow that occurs within a particular inhalation immediately after the particular exhalation to increase a volumetric rate of expulsion of $CO_2$, based on the one or more phase timing parameters and the determination whether the subject has completed the particular exhalation,
      wherein the adjustment of the pressurized flow includes adjusting, in a direction, a control parameter that affects the expulsion of $CO_2$ until an indication of a decrease in the expulsion of $CO_2$ and responsive to the decrease in the expulsion of $CO_2$, reversing the direction of adjustment to the control parameter.

2. The system of claim 1, wherein the inhalations have inspiratory periods, one of which is used as the control parameter, and
   wherein the control of the pressurized flow during the inhalations includes adjustments of the inspiratory periods based on the one or more breathing parameters.

3. The system of claim 2, wherein the one or more breathing parameters indicate a minute volume, and
   wherein the inspiratory periods are increased responsive to an increase of the minute volume over a period spanning multiple breaths.

4. The system of claim 1, wherein the one or more breathing parameters include one or more of a minute volume, end-tidal $CO_2$, transcutaneous $CO_2$, and an arterial blood gas measurement,
   wherein one or more values of the one or more breathing parameters indicate hypercapnia, and
   wherein the control of the pressurized flow during the inhalations includes adjustments of one or more of an inspiratory period, a peak flow, an inhalation pressure support level, and a flow shape such that the expulsion of $CO_2$ is increased.

5. The system of claim 1, wherein the volumetric rate of expulsion of $CO_2$ is determined for a first set of breathing cycles,
   wherein the control of the pressurized flow includes adjustments of the pressurized flow of breathable gas during a second set of breathing cycles to increase the volumetric rate of expulsion of $CO_2$ compared to the determined volumetric rate of expulsion of $CO_2$ for the first set of breathing cycles, and
   wherein the second set is subsequent to the first set.

6. A method to control respiratory therapy to a subject, wherein the respiratory therapy includes mechanical ventilation, the method being implemented using a pressure generator that provides a pressurized flow of breathable gas at a pressure level to an airway of the subject, one or more sensors, and one or more physical processors, the method comprising:
   generating, by the one or more sensors, output signals conveying information related to breathing of the subject, wherein the breathing includes inhalations and exhalations;
   determining, by the one or more physical processors, one or more phase timing parameters related to breathing phases of the subject based on the generated output signals, the one or more phase timing parameters comprising a moment and/or a duration related to the breathing phases;

determining, by the one or more physical processors, one or more breathing parameters of the subject based on the generated output signals, wherein the one or more breathing parameters indicate one or more of lung volume, tidal volume, and/or flow rate of the breathing of the subject;

determining, by the one or more physical processors, during the exhalations, whether the subject has completed a particular exhalation based on the one or more breathing parameters;

controlling, by the one or more physical processors, the pressurized flow of breathable gas in accordance with a respiratory therapy regimen such that the pressure level of the pressurized flow corresponds to an inspiratory positive airway pressure level during the inhalations and to an expiratory positive airway pressure level during the exhalations, adjusting, by the one or more physical processors, the pressurized flow that occurs within a particular inhalation immediately after the particular exhalation to increase a volumetric rate of expulsion of CO2 based on the phase timing parameters, and the determination whether the subject has completed the particular exhalation, wherein the adjusting of the pressurized flow includes adjusting, in a direction, a control parameter that affects the expulsion of CO2 until an indication of a decrease in the expulsion of CO2 and, responsive to the decrease in the expulsion of CO2, reversing the direction of adjustment to the control parameter.

7. The method of claim 6, wherein the inhalations have inspiratory periods, one of which is used as the control parameter, and
wherein the controlling the pressurized flow during the inhalations includes adjustments of the inspiratory periods based on the one or more breathing parameters.

8. The method of claim 7, wherein the one or more breathing parameters indicate a minute volume, and
wherein the inspiratory periods are increased responsive to an increase of the minute volume over a period spanning multiple breaths.

9. The method of claim 7, wherein the one or more breathing parameters include one or more of a minute volume, end-tidal $CO_2$, transcutaneous $CO_2$, and an arterial blood gas measurement,
wherein one or more values of the one or more breathing parameters indicate hypercapnia, and
wherein the controlling the pressurized flow during the inhalations includes adjustments of one or more of an inspiratory period, a peak flow, an inhalation pressure support level, and a flow shape such that the expulsion of $CO_2$ is increased.

10. The method of claim 6, wherein the volumetric rate of expulsion of $CO_2$ is determined for a first set of breathing cycles,
wherein the controlling the pressurized flow includes adjusting the pressurized flow of breathable gas during a second set of breathing cycles to increase the volumetric rate of expulsion of $CO_2$ compared to the determined volumetric rate of expulsion of $CO_2$ for the first set of breathing cycles, and
wherein the second set is subsequent to the first set.

11. A system configured to provide respiratory therapy to a subject through mechanical ventilation, the system comprising:
means for providing a pressurized flow of breathable gas at a pressure level to an airway of the subject;
means for generating output signals conveying information related to breathing of the subject, wherein the breathing includes inhalations and exhalations;
means for determining one or more phase timing parameters related to breathing phases of the subject based on the generated output signals, the one or more phase timing parameters comprising a moment and/or a duration related to the breathing phases;
means for determining one or more breathing parameters of the subject based on the generated output signals, wherein the one or more breathing parameters indicate one or more of lung volume, tidal volume, and/or flow rate of the breathing of the subject;
means for determining whether, during the exhalations, the subject has completed a particular exhalation based on the one or more breathing parameters;
means for controlling the pressurized flow of breathable gas in accordance with a respiratory therapy regimen such that the pressure level of the pressurized flow corresponds to an inspiratory positive airway pressure level during the inhalations and to an expiratory positive airway pressure level during the exhalations; and
means for adjusting the pressurized flow that occurs within a particular inhalation immediately after the particular exhalation to increase a volumetric rate of expulsion of $CO_2$ based on the one or more phase timing parameters, and the determination whether the subject has completed the particular exhalation,
wherein the adjustment of the pressurized flow includes adjusting, in a direction, a control parameter that affects the expulsion of $CO_2$ until an indication of a decrease in the expulsion of $CO_2$ and, responsive to the decrease in the expulsion of $CO_2$, reversing the direction of adjustment to the control parameter.

12. The system of claim 11, wherein the inhalations have inspiratory periods, one of which is used as the control parameter, and
wherein the means for controlling the pressurized flow is configured to adjust the inspiratory periods based on the one or more breathing parameters.

13. The system of claim 12, wherein the one or more breathing parameters indicate a minute volume, and
wherein the means for controlling the pressurized flow is configured to increase the inspiratory periods responsive to an increase of the minute volume over a period spanning multiple breaths.

14. The system of claim 12, wherein the one or more breathing parameters include one or more of a minute volume, end-tidal $CO_2$, transcutaneous $CO_2$, and an arterial blood gas measurement,
wherein one or more values of the one or more breathing parameters indicate hypercapnia, and
wherein the means for controlling the pressurized flow is configured to adjust one or more parameters of an inspiratory period, a peak flow, an inhalation pressure support level, and a flow shape such that the expulsion of $CO_2$ is increased.

15. The system of claim 11, wherein the volumetric rate of expulsion of $CO_2$ is determined for a first set of breathing cycles,
wherein the means for controlling the pressurized flow is configured to adjust the pressurized flow of breathable gas during a second set of breathing cycles to increase the volumetric rate of expulsion of $CO_2$ compared to the determined volumetric rate of expulsion of $CO_2$ for the first set of breathing cycles, and
wherein the second set is subsequent to the first set.

* * * * *